US012648793B2

(12) United States Patent
Fleming et al.

(10) Patent No.: US 12,648,793 B2
(45) Date of Patent: Jun. 9, 2026

(54) SUBCUTANEOUS IMPLANT REMOVAL DEVICE

(71) Applicant: Beth Fleming, Knoxville, TN (US)

(72) Inventors: Beth Fleming, Knoxville, TN (US); Kristopher C. Hall, Maryville, TN (US); Benjamin Nibali, Maryville, TN (US)

(73) Assignee: Beth Fleming, Knoxville, TN (US)

( * ) Notice: Subject to any disclaimer, the term of this patent is extended or adjusted under 35 U.S.C. 154(b) by 833 days.

(21) Appl. No.: 18/046,925

(22) Filed: Oct. 16, 2022

(65) Prior Publication Data

US 2023/0132741 A1 May 4, 2023

Related U.S. Application Data

(60) Provisional application No. 63/274,177, filed on Nov. 1, 2021.

(51) Int. Cl.
A61B 17/34 (2006.01)
A61B 17/3209 (2006.01)
(Continued)

(52) U.S. Cl.
CPC .... A61B 17/3468 (2013.01); A61B 17/32093 (2013.01); A61B 2017/00407 (2013.01); A61B 2017/320052 (2013.01)

(58) Field of Classification Search
CPC .......... A61B 17/3468; A61B 17/32093; A61B 17/52; A61B 17/505; A61B 2017/320052;
(Continued)

(56) References Cited

U.S. PATENT DOCUMENTS 4,570,613 A * 2/1986 Alkon ................... A61B 17/32
606/131
5,290,291 A 3/1994 Linden
(Continued)

FOREIGN PATENT DOCUMENTS

GB 2503059 A * 12/2013 ......... A61B 17/3468

OTHER PUBLICATIONS

Nexplanon (R) (etonogestrel implant) 68 mg Radiopaque: Clinical Training Program Slide Booklet; Copyright 2021 Organon group of companies; 56 pages.

(Continued)

*Primary Examiner* — Wesley G Harris
*Assistant Examiner* — Charles W Nichols
(74) *Attorney, Agent, or Firm* — Peter L. Brewer; Thrive IP

(57) ABSTRACT

A subcutaneous implant removal device designed to work with a variety of cylindrical implants. The implant removal device comprises a non-planar base. The non-planar base is dimensioned to be placed onto the epidermal surface of a patient's skin. The base has a proximal end and a distal end. When placed on the patient's skin, the proximal end slopes upward while the distal end slopes downward along the patient's skin. The subcutaneous implant removal device also includes a pinnacle. The pinnacle extends upward from the non-planar base and has a front face and a rear face. The front face of the pinnacle is dimensioned to receive a force from a thumb of a clinician, holding the removal device in place on the patient's skin during use. A method for removing a subcutaneous implant is also provided.

9 Claims, 8 Drawing Sheets

(51) Int. Cl.
| | |
|---|---|
| *A61B 17/00* | (2006.01) |
| *A61B 17/32* | (2006.01) |

(58) Field of Classification Search
CPC .. A61B 2017/320056; A61B 2090/036; A61B 17/88; A61B 17/90; A61M 37/0069; A61F 2/4603
USPC ...................................... 606/131; 62/91, 650
See application file for complete search history.

(56) References Cited

U.S. PATENT DOCUMENTS

| | | | | |
|---|---|---|---|---|
| 5,607,434 | A | * | 3/1997 | Alvino ................... A61B 17/50 606/210 |
| D716,498 | S | * | 10/2014 | Wolff ........................... D24/143 |
| 11,484,504 | B2 | | 11/2022 | Schneeberger et al. |
| 11,497,834 | B1 | | 11/2022 | Buell et al. |
| 11,504,035 | B2 | | 11/2022 | Kintz et al. |
| 2004/0087959 | A1 | * | 5/2004 | Parmigiani ............ A61B 17/32 606/85 |
| 2014/0276928 | A1 | * | 9/2014 | Vanderpool .............. A61B 5/29 606/129 |
| 2020/0078035 | A1 | * | 3/2020 | Britland ................. B33Y 80/00 |
| 2021/0093466 | A1 | * | 4/2021 | Bravman .............. A61F 2/4637 |
| 2022/0125591 | A1 | * | 4/2022 | Rivera, Jr. ............. A61B 17/92 |
| 2022/0370437 | A1 | | 11/2022 | Kim et al. |
| 2022/0370529 | A1 | | 11/2022 | Leverett |

OTHER PUBLICATIONS

Excerpts taken from www.nexplanon.com; Accessed Dec. 5, 2022; 4 pages.
Excerpts take from www.supprelnila.com; Accessed Dec. 5, 2022; 2 pages.

* cited by examiner

400

410
Locate a Cylindrical, Subcutaneous Implant
Below the Skin of a Patient

415
Provide an Incision Guide

420
Place the Base of the Incision Guide
Proximate a First End of the Subcutaneous Implant 425
Provide an Implant Removal Guide 430
Place the Body of the Implant Removal Guide
Proximate a Second End of the Subcutaneous Implant

400

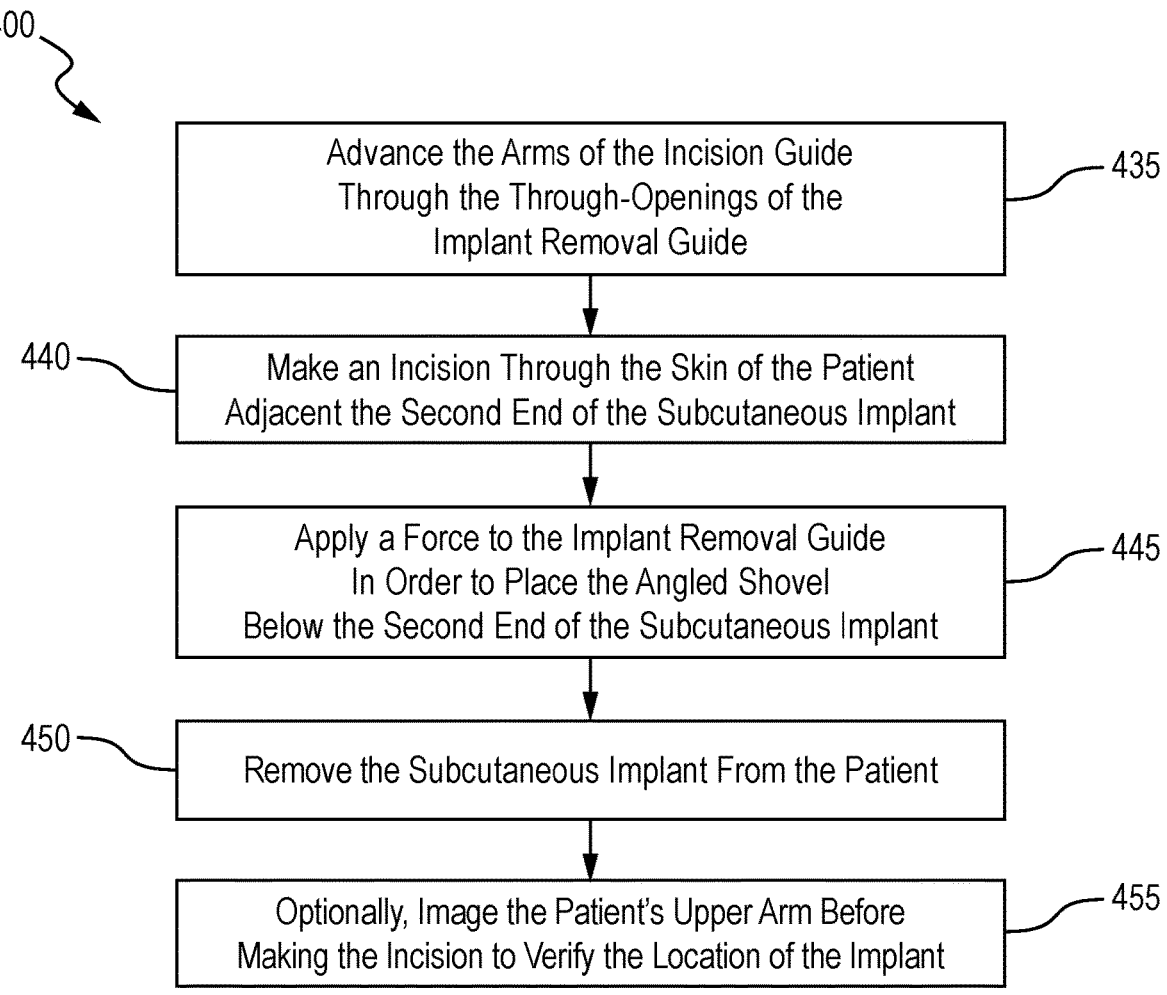

| | |
|---|---|
| Advance the Arms of the Incision Guide Through the Through-Openings of the Implant Removal Guide | 435 |

↓

| | |
|---|---|
| Make an Incision Through the Skin of the Patient Adjacent the Second End of the Subcutaneous Implant | 440 |

↓

| | |
|---|---|
| Apply a Force to the Implant Removal Guide In Order to Place the Angled Shovel Below the Second End of the Subcutaneous Implant | 445 |

↓

| | |
|---|---|
| Remove the Subcutaneous Implant From the Patient | 450 |

↓

| | |
|---|---|
| Optionally, Image the Patient's Upper Arm Before Making the Incision to Verify the Location of the Implant | 455 |

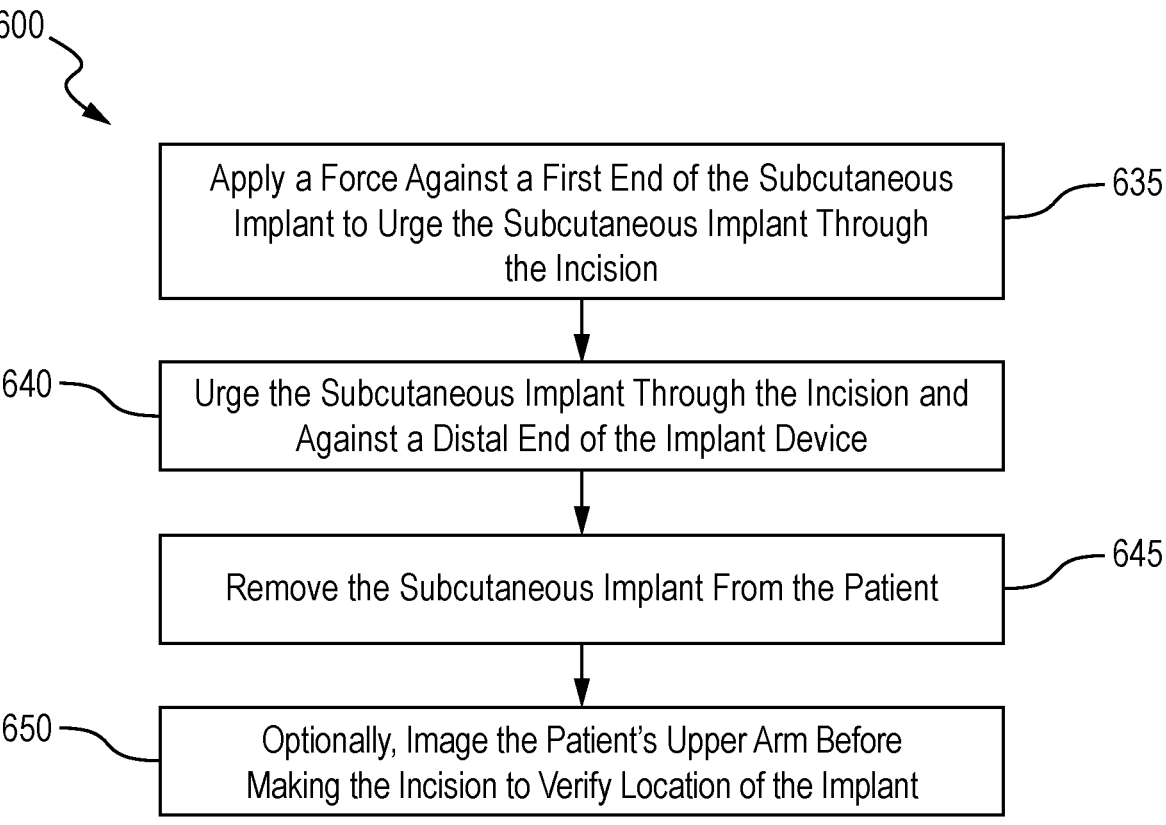

| | |
|---|---|
| Apply a Force Against a First End of the Subcutaneous Implant to Urge the Subcutaneous Implant Through the Incision | 635 |
| Urge the Subcutaneous Implant Through the Incision and Against a Distal End of the Implant Device | 640 |
| Remove the Subcutaneous Implant From the Patient | 645 |
| Optionally, Image the Patient's Upper Arm Before Making the Incision to Verify Location of the Implant | 650 |

FIG. 6B

SUBCUTANEOUS IMPLANT REMOVAL DEVICE

CROSS REFERENCE TO RELATED APPLICATIONS

This application claims the benefit of U.S. Ser. No. 63/274,177 filed Nov. 1, 2021. That application is entitled "Subcutaneous Implant Removal Device" and is incorporated herein in its entirety by reference.

STATEMENT REGARDING FEDERALLY SPONSORED RESEARCH OR DEVELOPMENT

Not applicable.

BACKGROUND OF THE INVENTION

This section is intended to introduce various aspects of the art, which may be associated with exemplary embodiments of the present disclosure. This discussion is believed to assist in providing a framework to facilitate a better understanding of particular aspects of the present disclosure. Accordingly, it should be understood that this section should be read in this light, and not necessarily as admissions of prior art.

Field of the Invention

The present invention relates to the delivery of medicament to a patient through a subdermal implant. More specifically, the invention relates to a device used in the removal of a pharmaceutical object implanted under the skin of a patient. The invention further relates to a method for removing an implant from a patient.

Technology in the Field of the Invention

A medical implant is a device that can be placed inside a patient's body or affixed onto the skin of a patient. Medical implants that are placed just under the skin are referred to as subdermal implants.

Subdermal implants can be used for a variety of treatments. One example of an implant is a spinal cord stimulator. A spinal cord stimulator is an implanted device that sends low levels of electricity directly into the spinal cord of the patient to relieve pain. Another example is a glucose level sensor. The glucose level sensor is implanted just under the skin during an outpatient procedure. After it is implanted, the glucose level sensor measures glucose levels for up to 90 days.

One category of medical implants represents devices that are placed subcutaneously for a period of time for the purpose of delivering medication or treatment. For example, subdermal implants have been used to provide histrelin acetate, which is a hormone suppression drug provided to children. The drug is prescribed by a pediatric endocrinologist following a diagnosis of central precocious puberty, or CPP. The drug may be delivered subcutaneously using a device called Supprelin® LA. Supprelin® LA is available from Endo Pharmaceuticals Solutions Inc. of Malvern, Pennsylvania. Another device is one that is used to provide etonogestrel, which is a birth control medication, or contraceptive. Etonogestrel may be provided as an implant by N.V. Organon of Oss, Netherlands, sold under the mark Nexplanon®. The implant is placed just under the skin of a biologically female patient, typically up under the patient's non-dominant arm.

In the case of both Supprelin® LA and Nexplanon®, the implant is removed after a period of time, usually between six months and three years. The current process for removing subcutaneous implants involves the use of common medical tools and techniques that have a broad range of applications. Such tools may include a topical anesthetic that is applied to the incision site. Examples of such an anesthetic include povidone-iodine, lidocaine, benzocaine, and chlorhexidine. Such tools also included a sterile scalpel (e.g. 15 blade), sterile forceps, 4×4 sterile gauze, butterfly stitches, and a pressure bandage.

After cleaning the skin and applying the local anesthetic, a clinician uses the scalpel to make a small incision, often 2 to 5 mm in length, into the skin. The incision is made at one end of the subcutaneous implant and cuts to the depth of the implant. Ideally, an end of the implant protrudes through the incision and can be easily removed. However, forceps are sometimes needed when the implant is not visible to hold the end of the implant and pull the implant through the incision. The gauze is used throughout the procedure to clean blood from the incision. Following removal of the implant, butterfly stiches and the pressure bandages are placed over the incision site for healing.

The size of various subcutaneous implants differs; however, many share a common shape. The Nexplanon® implant is a solid cylinder having a 2 mm diameter and a length of 4 cm. The Supprelin® LA implant has a similar shape with a 3 mm diameter and a length of 3.5 cm. Because of the implant's small, cylindrical size, the implant tends to move around under the patient's skin. This is a phenomenon known as migration.

The mobility of the implant combined with its flexibility complicates the removal procedure. There have been reported cases of peripheral nerve injury and injury to blood vessels as a result of the clinician "chasing" the implant under the skin during attempted removal. Some case reports have described implant-related injuries to the median, ulnar, and medial antebrachial cutaneous nerves.

Accordingly, a medical device is needed that will limit the motion of the subdermal implant during the removal process, thereby enabling the clinician to use the scalpel to cut directly over the implant end to access and readily remove the implant. An improved method of removing a subdermal implant is also needed, wherein migration of a cylindrical implant is restricted.

BRIEF SUMMARY OF THE INVENTION

A subcutaneous implant removal device is first provided herein. The implant removal device is designed to work with a variety of cylindrical implants. The device is ideally designed to assist in the removal of subcutaneous implants with diameters ranging from approximately 2 to 4 mm and lengths ranging between 2 cm to 6 cm.

In one aspect, the subcutaneous implant removal device comprises two components. These represent an incision guide and an implant removal guide.

The incision guide first comprises a base. The base has a proximal end and a distal end. The incision guide also has at least two elongated arms, with the arms extending from the base in parallel relationship. A gap is preserved between the two arms. In one aspect, each of the elongated arms is between 3 cm and 10 cm in length, while the gap between the elongated arms is 2 cm to 6 cm in length.

Preferably, each of the arms has an outer face opposite the gap. The outer face of each arm comprises ratchet teeth.

The implant removal guide comprises a body having a proximal side and an opposing distal side. The implant removal guide also includes a pair of openings. The pair of openings extend through the body, with each opening dimensioned to receive a respective arm from the incision guide. Additionally, the implant removal guide has an angled shovel. The angled shovel resides along the proximal side of the body and is dimensioned to receive an end of the implant.

Each of the openings includes a ratchet lever. The ratchet levers are configured to releasably hold the respective arms in place along the body as the arms are advanced through the openings. Thus, the length of the arms is adjustable relative to the implant removal guide, depending on the length of the implant being removed. Preferably, each of the at least two arms and each of the openings in the body of the implant removal guide are fabricated from nylon, polycarbonate, or other thermoplastic material.

In another arrangement, a subcutaneous implant removal device is provided that comprises only a single component. The removal device first comprises a non-planar base. The non-planar base is dimensioned to be placed onto an epidermal surface of a patient's skin.

The non-planar base has a proximal end and an opposite distal end. When placed on the patient's skin, the proximal end slopes upward at an angle of between 10 and 40 degrees, inclusive. At the same time, the distal end slopes downward at an angle of between 5 and 15 degrees, inclusive.

The subcutaneous implant removal device also includes a pinnacle. The pinnacle extends upward from the non-planar base. The pinnacle has a front face and a rear face. Of interest, the front face of the pinnacle is dimensioned to receive a force from a thumb of a clinician. The force is primarily downward, holding the subcutaneous implant removal device in place on the patient's skin during use.

The pinnacle comprises a pair of arms. These represent a first arm on a first side of the non-planar base, and a second arm on a second side of the base opposite the first arm. A bridge connects the first arm, the second arm, and the non-planar base. The distal end of the base defines a concave intersection between the bridge and the non-planar base forming an obtuse angle. At the same time, a connection between the rear face and the non-planar base defines a concave intersection that forms an acute angle.

In a preferred embodiment, the subcutaneous implant removal device comprises a single piece fabricated from a polycarbonate material. The non-planar base is between 3 cm and 6 cm in length while the pinnacle is between 1 cm and 3 cm in height.

Methods of removing a subcutaneous implant are also provided herein. In a first embodiment, the method comprises locating an implant below the skin of a patient. The implant is preferably a cylindrical implant designed to deliver a pharmaceutical substance to the patient.

In one aspect, the pharmaceutical substance is in the form of a short, cylindrical device that is injected into and under the skin of the patient. The implant may be, for example, 2 cm to 5 cm in length and is designed to go into the patient's upper arm, and under the skin of the arm.

The method also includes providing an incision guide. The incision guide is in accordance with the incision guide outlined above. The method then comprises placing the base of the incision guide proximate a first end of the subcutaneous implant.

The method also includes providing an implant removal guide. The implant removal guide is in accordance with the implant removal guide outlined above. The method then comprises placing the body of the implant removal guide proximate a first end of the subcutaneous implant.

The method further comprises advancing the arms of the incision guide through the respective openings of the implant removal guide. The ratchet levers of the implant removal guide are configured to releasably hold the respective arms in place along the body as the arms are advanced through the openings. The arms are advanced until they extend through the openings, placing the implant removal guide at the second end of the subcutaneous implant.

Next, the method includes making an incision through the skin of the patient. The incision is made above the second end of the subcutaneous implant, down to a depth of the second end. The method then includes applying a force to the implant removal guide in order to place an angled shovel below the second end of the subcutaneous implant. This may involve further advancing the arms through the respective openings.

Additionally, the method comprises removing the subcutaneous implant from the patient. This may be done, for example, by using a pair of forceps once the second end of the implant is exposed.

A second method of removing a subcutaneous implant is also provided herein. In one aspect, the method first comprises:

locating an elongated implant below the skin of a patient; and placing an implant removal device onto the skin proximate the implant.

The implant removal device includes a non-planar base having a proximal end and a distal end. The proximal end slopes upward at an angle of between 10 and 40 degrees, inclusive, while the distal end slopes downward at an angle of between 5 and 15 degrees, inclusive. The implant removal device also has a pinnacle. The pinnacle extends upward from the non-planar base, with the pinnacle having a front face and a rear face.

The implant removal device is placed onto the patient's skin proximate a second end of the subcutaneous implant. A clinician then makes an incision through the skin of the patient above the second end of the subcutaneous implant, down to a depth of the second end.

The method next includes applying a downward force to the implant removal device. This serves to hold the implant removal device in place along the patient's skin. In one aspect, applying a downward force comprises the clinician pressing a thumb against the front face of the pinnacle. At the same time, the clinician applies a force against a first end of the subcutaneous implant. The method then includes urging the subcutaneous implant through the incision and against the distal end of the base.

The method further comprises removing the subcutaneous implant from the patient. This may be done by using forceps. In a preferred arrangement, the subcutaneous implant is a pharmaceutical delivery implant. In one aspect, the subcutaneous implant is placed within the patient's upper arm. In one arrangement, the method further comprises imaging the patient's upper arm before making the incision in order to verify a location of the subcutaneous implant.

DESCRIPTION OF THE DRAWINGS

So that the manner in which the present inventions can be better understood, certain illustrations, charts, and/or flow charts are appended hereto. It is to be noted, however, that the drawings illustrate only selected embodiments of the inventions and are therefore not to be considered limiting of scope, for the inventions may admit to other equally effective embodiments and applications.

FIGS. 4A and 4B together provide a flow chart showing steps for a method of removing a subcutaneous implant, in a first embodiment.

FIGS. 6A and 6B together provide a flow chart showing steps for a method of removing a subcutaneous implant, in a second embodiment.

DETAILED DESCRIPTION OF SELECTED SPECIFIC EMBODIMENTS

Figure 1:
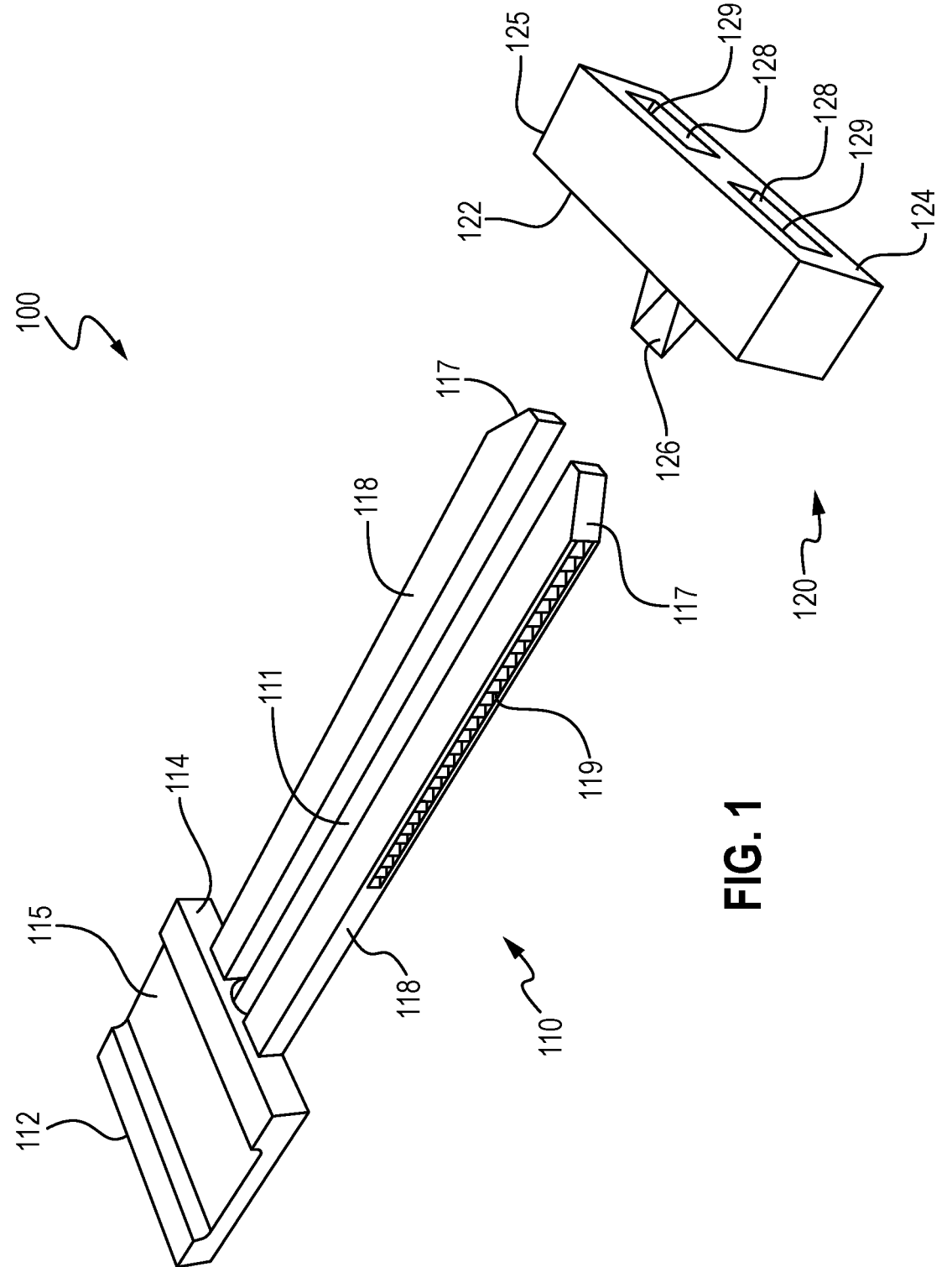
FIG. 1 is a perspective view of a subcutaneous implant removal device of the present invention, in a first embodiment. In this embodiment, the subcutaneous implant removal device comprises two distinct components.

The novel features characteristic of the embodiments of the present application are set forth in the appended claims. However, the embodiments themselves and further objectives and advantages thereof, will best be understood by reference to the following detailed description when read in conjunction with the accompanying drawings, wherein:

FIG. 1 is a perspective view of a subcutaneous implant removal device 100 of the present invention, in one embodiment. The subcutaneous implant removal device 100 comprises two separate parts. These represent an incision guide 110 and an implant removal guide 120.

The incision guide 110 comprises a base 115. The base 115 has a proximal end 112 and a distal end 114. The base 115 is generally configured to be held in the hand of a clinician during the removal of an implant from the skin of a patient. The base 115 may be fabricated from any material, but preferably from a material that can be pre-packaged in a sterile condition, such as metal.

The base 115 preferably has a flat or gently concave under-surface. The under-surface is configured to be placed against the skin of a patient, and preferably under the upper arm of the patient.

Extending from the distal end 114 of the base 115 is a pair of arms 118. The pair of arms 118 extend out from the base 115 in parallel relation. A gap 111 is preserved between the pair of arms 118. The arms 118 are preferably spaced-apart at about one to four centimeters, meaning the gap is 1 cm to 4 cm wide. Each arm 118 is preferably approximately 4 cm to 10 cm in length and co-terminates at an angled tip 117.

At opposing sides of the pair of arms 118 are so-called one-way ramps 119. The one-way ramps 119 represent ratchet teeth and are similar in style to the teeth of a cable-tie or "zip tie." In this instance, the one-way ramps 119 are preferably recessed into the opposing sides of the pair of arms 118, but this is an optional feature of the present embodiment.

In operation, the body 115 of the incision guide 110 is placed on top of the skin of the patient, over a first end of a subcutaneous implant. The pair of arms 118 are then placed along the length of the subcutaneous implant. The arms 118 are dimensioned to extend beyond the length of the implant and are positioned parallel to the implant, with one arm 118 on each side of the subcutaneous implant. This means that the subcutaneous implant resides within and immediately below the gap 111.

Referring now to the implant removal guide 120, the implant removal guide 120 also comprises a body 125. The body 125 has a distal face 122 and a proximal face 124. Extending through the body 125 from the distal face 122 to the proximal face 124 is a pair of through-openings 128. Each through-opening 128 is dimensioned to slidably receive a respective arm 118 of the incision guide 110.

Each through-opening 128 comprises a ratchet lever 129. The ratchet levers 129 catch the one-way ratchet teeth 119 of the arms 118 as the arms 118 slide through each of the respective through-openings 128. In this way, the arms 118 are locked in place along the implant removal guide 120. The length of the subcutaneous implant, which resides immediately below the gap 111 during removal, dictates a length to which the arms 118 slidably engage and subsequently lock into place along the implant removal guide 120. Simultaneously tripping the ratchet levers 129 will release the arms 118, allowing the arms 118 to be slidably removed from the body 125 of the implant removal guide 120.

The proximal face 122 of the body 125 includes an angled shovel 126. The angled shovel 126 forms a wedge that fits slightly underneath a second end of the subcutaneous implant. Once the angled shovel 126 is in place and the arms 118 are locked into the body 125, the clinician will use a scalpel to make an incision directly over the end of the subcutaneous implant that is resting on the angled shovel 126. As the incision reaches a depth of the subcutaneous implant, the angled shovel 126 will direct the subcutaneous implant end through the incision.

Figure 2:
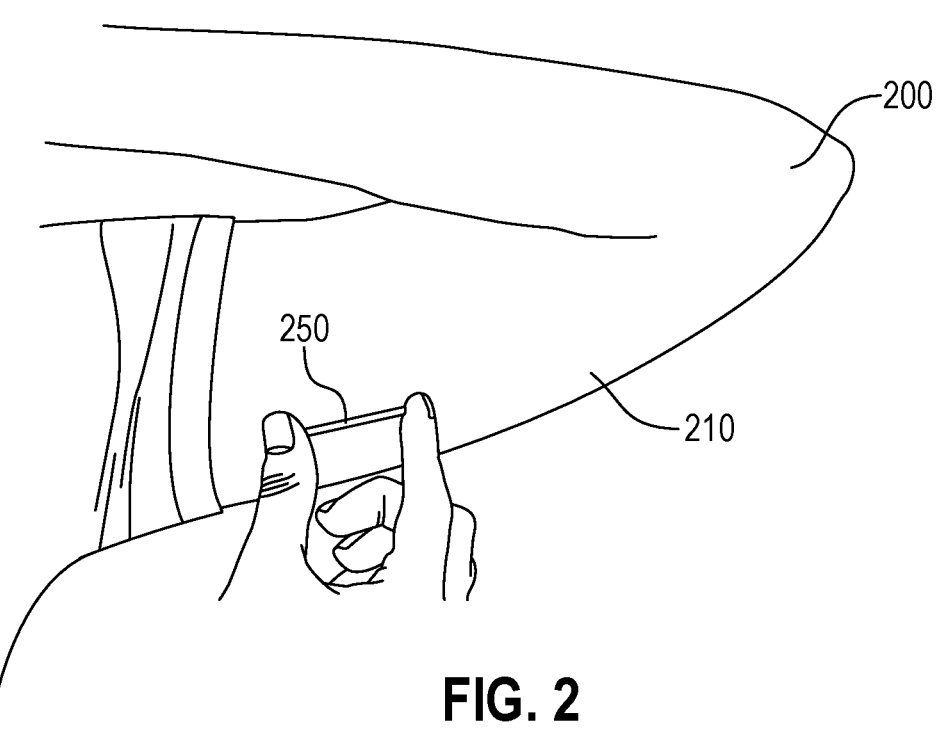
FIG. 2 is a perspective view of a patient's arm, and specifically, the upper under-arm portion of the patient. A pharmaceutical implant is being held adjacent to a point of intended implant.

FIG. 2 is a perspective view of a patient's arm 200. Specifically, the patient's upper, under-arm portion 210 is shown. Of interest, an implantable pharmaceutical device 250 is being held adjacent to a point of intended implant in the upper, under-arm 210. The implantable pharmaceutical device 250 may comprise, for example, a hormone suppression drug or a contraceptive.

Figure 3:
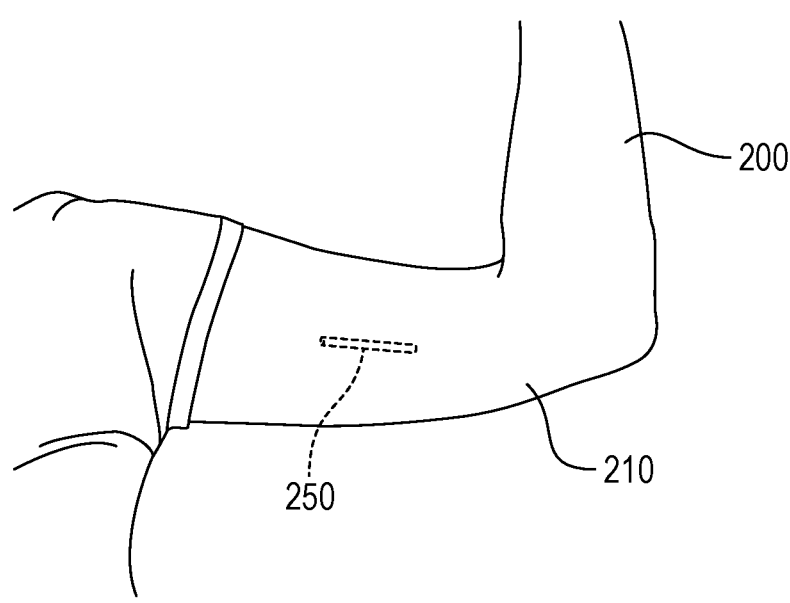
FIG. 3 is another perspective view a patient's arm, and specifically the upper arm. Here, the pharmaceutical device has been implanted into the under-arm portion of the patient, under the patient's skin.

FIG. 3 is another perspective view of the patient's arm 200. The upper, under-arm portion 210 of the patient is again emphasized. Here, the implantable pharmaceutical device 250 has been implanted into the upper, under-arm portion 210 of the patient.

Figure 4A:
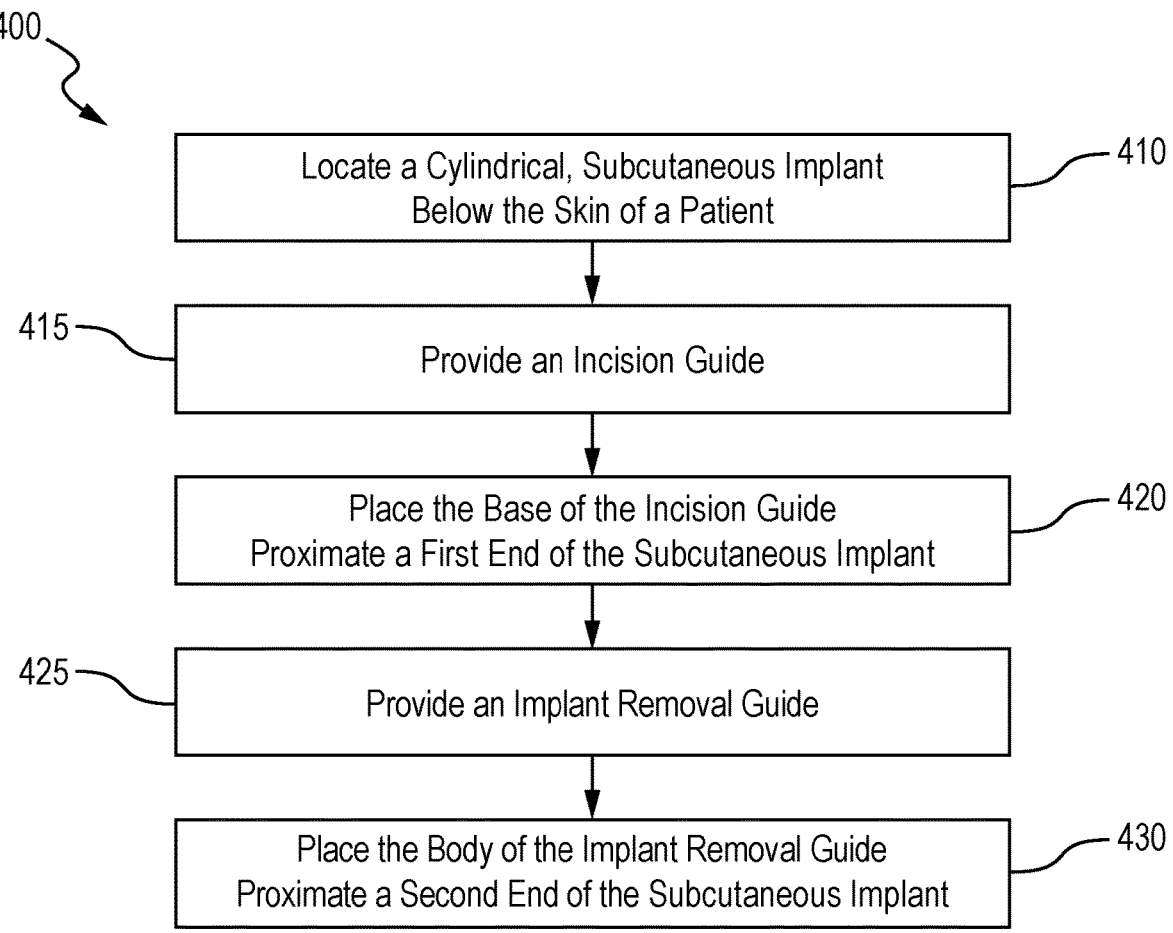

Using the subcutaneous implant removal device 100 described above, a method 400 of removing the subcutaneous implant 250 is also provided herein. Steps for performing the method 400 are provided in FIGS. 4A and 4B, together, as a single flow chart.

In one embodiment, the method 400 first comprises locating a subcutaneous implant below the skin of a patient. Locating means finding, which may be done through palpation of the patient's skin. This step is shown in Box 410 of FIG. 4A.

The subcutaneous implant is preferably a cylindrical implant designed to deliver a pharmaceutical substance to the patient. Ideally, the implant resides immediately below the skin of the patient and can be quickly located by the clinician without need of imaging equipment.

In one aspect, the pharmaceutical substance is in the form of a short, cylindrical device that is injected into and under the skin of the patient. In one aspect, the implant is 2 cm to 5 cm in length and is designed to go into the patient's upper arm, and under the arm.

The method 400 next includes providing an incision guide. This is provided at Box 415. The incision guide is in accordance with the incision guide 110 outlined above. In this respect, the incision guide comprises:

a base having a proximal end and a distal end; and at least two elongated arms extending from the distal end of the base in parallel relationship, preserving a gap there between.

Preferably, each of the arms has an outer face opposite the gap. The outer face comprises ratchet teeth. The method 400 then comprises placing the base of the incision guide proximate a first end of the subcutaneous implant but on the skin. This is indicated at Box 420.

Next, the method 400 includes providing an implant removal guide. This is seen at Box 425. The implant removal guide is in accordance with the implant removal guide 120 outlined above. In this respect, the implant removal guide comprises:

a body having a proximal side and an opposing distal side;

a pair of openings extending through the body, with each opening dimensioned to receive a respective arm from the incision guide; and an angled shovel along the proximal side of the body, the angled shovel being dimensioned to receive an end of the implant opposite the base of the incision guide.

The method 400 then comprises placing the body of the implant removal guide proximate a second end of the subcutaneous implant. This is provided at Box 430 of FIG. 4A.

The method 400 further comprises advancing the arms of the incision guide through the respective through-openings of the implant removal guide. This is indicated at Box 435 of FIG. 4B. The ratchet levers of the implant removal guide are configured to engage the ratchet teeth of the respective arms and releasably hold the respective arms in place along the body as the arms are advanced through the openings. The arms are advanced through the respective openings until the body of the implant removal guide is at the second end of the implant.

Next, the method 400 includes making an incision through the skin of the patient. This is shown at Box 440. The incision is made above the second end of the subcutaneous implant, down to a depth of the second end. The method 400 then includes applying a force to the implant removal guide in order to place the angled shovel below the second end of the subcutaneous implant. This is seen at Box 445. This helps keep the implant from migrating during removal. It is noted that the steps of Boxes 440 and 445 may be reversed, or may be done simultaneously.

Additionally, the method 400 comprises removing the subcutaneous implant from the patient. This step is provided at Box 450. The step of Box 450 may be done, for example, by using a pair of forceps. The incision guide holds the implant in place during removal.

In some cases, the clinician may not be able to locate the implantable pharmaceutical device 250, shown in FIGS. 2 and 3, solely through palpation. In this instance, it may be necessary to locate the implantable pharmaceutical device 250 through imaging. This is indicated at Box 455. Imaging may include, for example, an X-Ray, a CT scan, or an MRI.

Figure 5A:
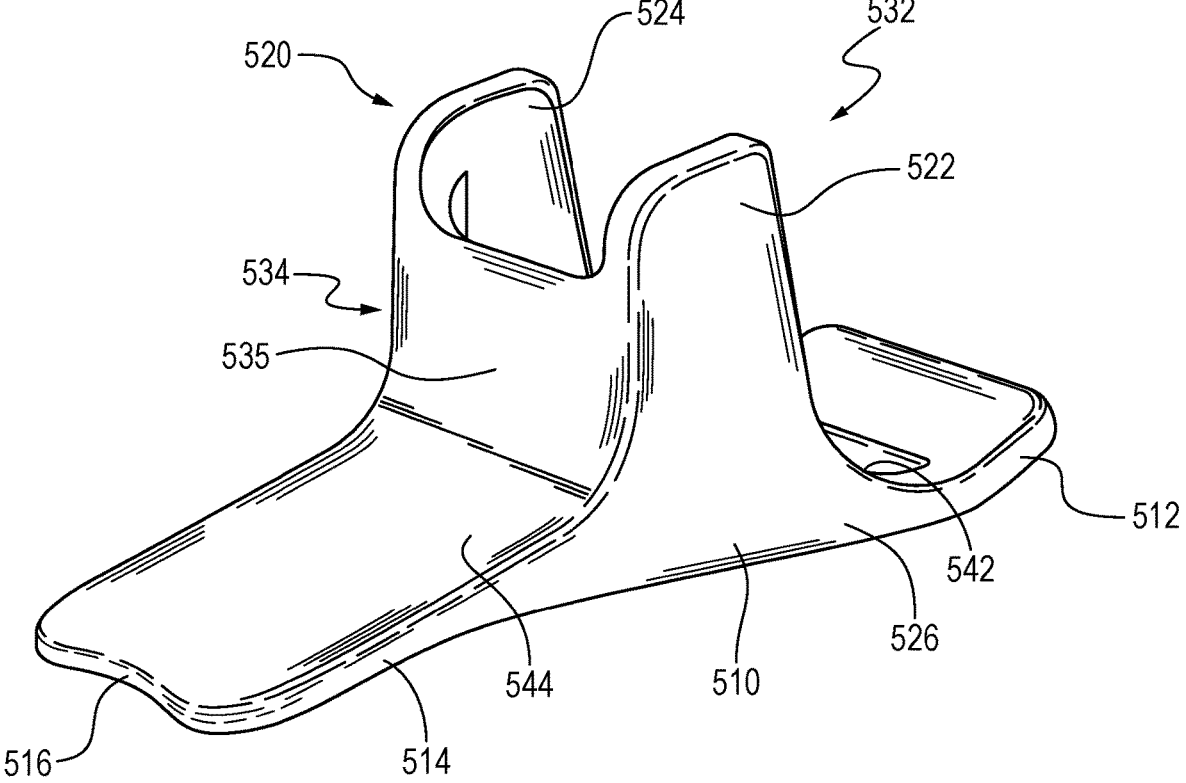
FIG. 5A is a perspective view of a subcutaneous implant removal device of the present invention, in a second embodiment. In this embodiment, the removal device comprises a single component.

FIG. 5A is a perspective view of a subcutaneous implant removal device 500 of the present invention, in a second embodiment. In this embodiment, the subcutaneous implant removal device 500 comprises a single component. The subcutaneous implant removal device 500 is designed to be used for removal of a subdermal implant, such as the implantable pharmaceutical device 250 of FIG. 2. Typically, the implantable pharmaceutical device 250 defines an elongated cylindrical body.

Figure 5B:
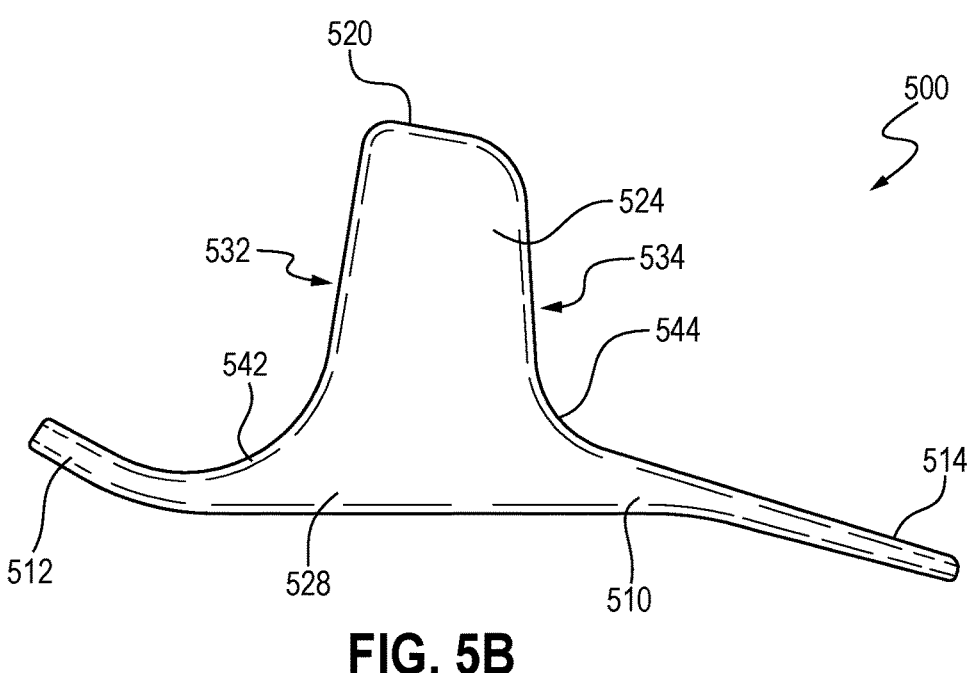
FIG. 5B is a side view of the implant removal device of FIG. 5A.
Figure 5C:
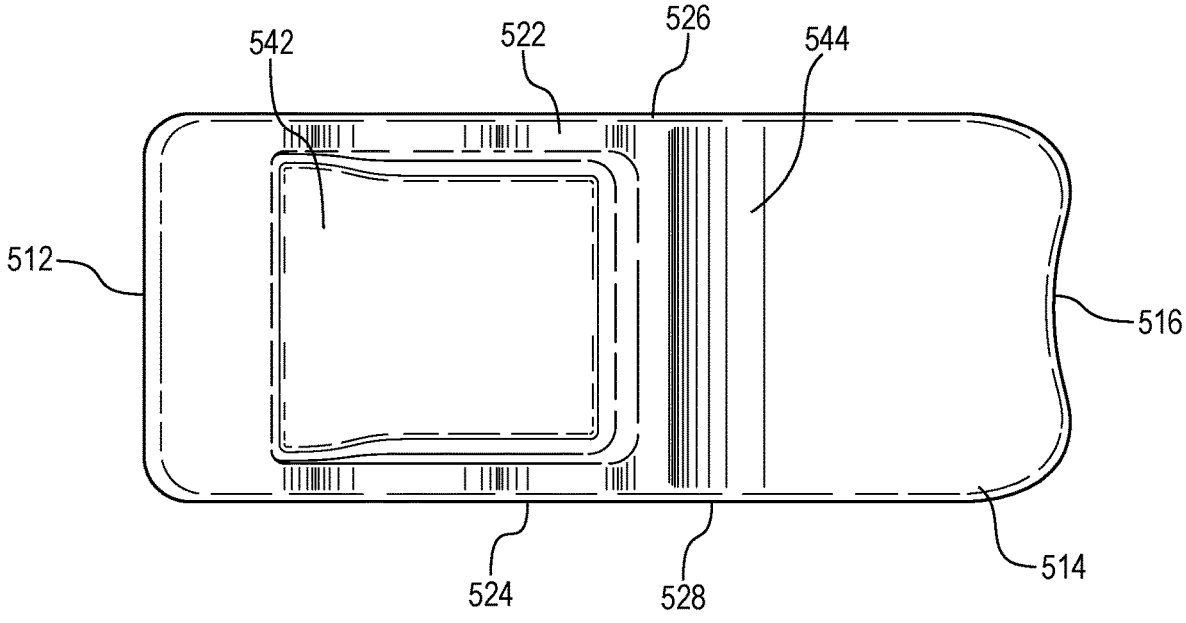
FIG. 5C is a top view of the implant removal device of FIG. 5A.

FIG. 5B is a side view of the subcutaneous implant removal device 500 of FIG. 5A. FIG. 5C is a top view of the implant removal device 500 of FIG. 5A. The implant removal device 500 will be discussed with respect to FIGS. 5A-5C, together.

The subcutaneous implant removal device 500 first comprises a base 510. As seen best in FIG. 5B, the base 510 is non-planar. The non-planar base 510 is dimensioned to be placed onto the surface of a patient's skin.

The base 510 has a proximal end 512 and a distal end 514. When placed on the patient's skin, the proximal end 512 slopes upward at an angle of between 10 and 40 degrees, inclusive. At the same time, the distal end 514 slopes downward at an angle of between 5 and 15 degrees, inclusive.

The subcutaneous implant removal device 500 also includes a pinnacle 520. The pinnacle 520 extends upward from the non-planar base 510. The pinnacle 520 has a front face 532 and a rear face 534. Of interest, the front face 532 of the pinnacle 520 is dimensioned to receive a force from a thumb of a clinician. The force is primarily downward, holding the removal device 500 in place on the patient's skin during use.

The pinnacle 520 comprises a pair of arms. These represent a first arm 522 on a first side 526 of the non-planar base 510, and a second arm 524 on a second side of the non-planar base 510 opposite the first arm 522. A bridge 535 connects the first arm 522, the second arm 524, and the non-planar base 510.

In a preferred embodiment, the subcutaneous implant removal device 500 comprises a single piece, fabricated from a polycarbonate material. The base 510 is between 3 cm and 6 cm in length while the pinnacle 520 is between 1 cm and 3 cm in height.

In a preferred arrangement, the bridge 535 defines a concave intersection 544 between the arms 522, 524 and the non-planar base 510 forming an obtuse angle. At the same time, a connection 542 between the rear face 534 and the non-planar base 510 defines a concave intersection that forms an acute angle. Optionally, the distal end 514 of the base 510 comprises an indentation 516. The indentation 516 is configured to receive a leading end of the elongated cylindrical body of the implantable pharmaceutical device 250.

Figure 6A:
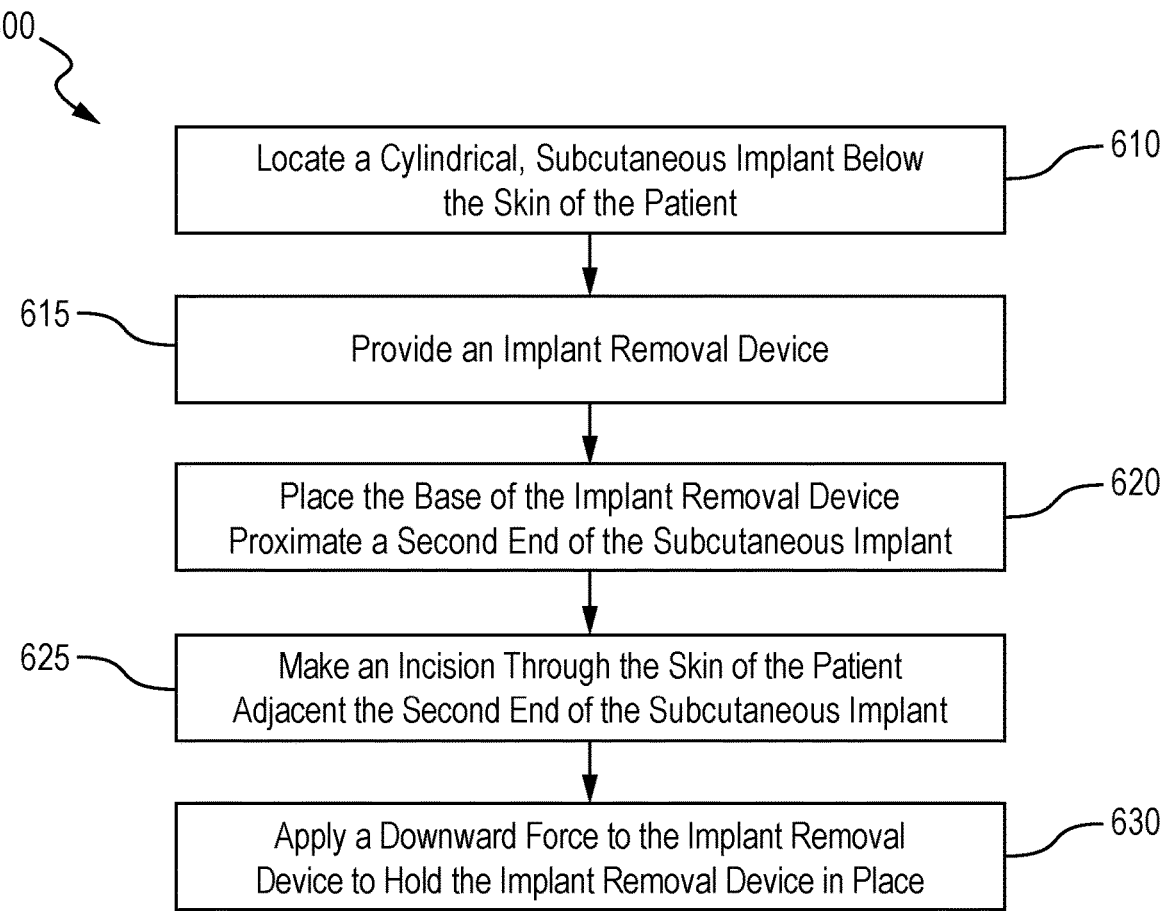

Using the subcutaneous implant removal device 500 described above, a method 600 of removing a subcutaneous implant is also provided herein. This is a second embodiment. Steps for performing the method 600 are provided in FIGS. 6A and 6B, together, as a single flow chart.

The method 600 first comprises locating an implant below the skin of a patient. Locating means finding, which may be done through palpation of the patient's skin. This step is shown in Box 610 of FIG. 6A.

The implant is preferably a cylindrical implant designed to deliver a pharmaceutical substance to the patient. Ideally, the implant resides immediately below the skin and can be quickly located by the clinician without need of imaging equipment.

In one aspect, the pharmaceutical substance is in the form of a short, cylindrical device that is injected into and under the skin. In one aspect, the implant is 2 cm to 5 cm in length and is designed to go into the patient's upper arm, and under the skin.

The method 600 next includes providing a subcutaneous implant removal device. This is provided at Box 615. The implant removal device is in accordance with the subcutaneous implant removal device 500 discussed above. In this respect, the implant removal device comprises:

a non-planar base having a proximal end and a distal end; and a pinnacle extending upward from the non-planar base, with the pinnacle having a front face and a rear face.

In this arrangement, the proximal end of the base slopes upward at an angle of between 10 and 40 degrees, inclusive, while the distal end slopes downward at an angle of between 5 and 15 degrees, inclusive. The base is dimensioned to reside on an epidermal surface of the patient. At the same time, the front face of the pinnacle is dimensioned to receive a force from a thumb of a clinician.

Next, the method 600 includes placing the base of the implant removal device proximate a second end of the subcutaneous implant. This is provided at Box 620 of FIG. 6A.

Next, the method 600 includes making an incision through the skin of the patient. This is shown at Box 625. The incision is made above the second end of the subcutaneous implant, down to a depth of the second end. The method 600 then includes applying a force to the implant removal device in order to place a distal end of the base below the second end of the subcutaneous implant. This is seen at Box 630. The force is a downward force and helps keep the implant from migrating. As with steps 440 and 445, steps 625 and 630 may be reversed or may be carried out simultaneously.

Additionally, the method 600 comprises applying a force against a first end of the implant. The first end of the implant is opposite the second end. This is provided at Box 635.

Further, the method 600 comprises urging the implant through the incision and against the distal end of the base. This is provided at Box 640. This is done by the clinician simultaneously:

placing a thumb against the front face of the pinnacle, while applying the force against the first end of the subcutaneous implant.

The downward force applied to the first end of the implant removal device can be used to pivot the implant removal device. The first end moves down while the second end flips up. This lifts the implant up through the incision. The face urges the second end of the implant onto the concave surface at the distal (or second) end of the implant removal device, and with travel limited by the bridge.

The method 600 then includes removing the subcutaneous implant from the patient. This step is provided at Box 645. The step of Box 645 may be done, for example, by using a pair of forceps.

As noted in connection with method 400, in some cases the clinician may not be able to locate the implantable pharmaceutical device 250 solely through palpation. In this instance, it may be necessary to locate the device through imaging. This is indicated at Box 650. Imaging may include, for example, an X-Ray, a CT scan, or an MRI.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application.

In the claims which follow, the word "comprising" is used in its inclusive sense and does not exclude other elements being present. The indefinite articles "a" and "an" before a claim feature do not exclude more than one of the features being present. Each one of the individual features described here may be used in one or more embodiments and is not, by virtue only of being described here, to be construed as essential to all embodiments as defined by the claims.

We claim:

1. A method of removing a subcutaneous implant, comprising:

locating an elongated subcutaneous implant below a skin of a patient;

providing an implant removal device, comprising:

a non-planar base having a proximal end and a distal end, wherein the proximal end slopes upward at an angle of between 10 and 40 degrees, inclusive while the distal end slopes upward at an angle of between 5 and 15 degrees, inclusive and a pinnacle extending upward from the non-planar base intermediate the proximal end and the distal end, with the pinnacle having a front face and a rear face; placing the non-planar base of the implant removal device onto the skin of the patient such that the proximal end of the non-planar base is proximate a leading end of the elongated subcutaneous implant;

making an incision through the skin of the patient above the leading end of the elongated subcutaneous implant, down to a depth of the leading end;

applying a downward force to the implant removal device while also applying a force against a trailing end of the elongated subcutaneous implant;

urging the leading end of the elongated subcutaneous implant through the incision and against the proximal end of the non-planar base; and removing the elongated subcutaneous implant from the patient.

2. The method of claim 1, wherein the elongated subcutaneous implant is a pharmaceutical delivery implant.

3. The method of claim 2, wherein applying a downward force to the elongated implant removal device comprises a clinician pressing a thumb against the front face of the pinnacle.

4. The method of claim 3, wherein:

the implant removal device is fabricated from a polycarbonate material; and the pharmaceutical delivery implant comprises a hormone suppression drug or a contraceptive.

5. The method of claim 3, wherein: the pinnacle further comprises:

a first arm on a first side of the non-planar base; inclusive, while the distal end of the base slopes downward at an angle of between 5 and 15 degrees, inclusive; and the base is non-planar;

and wherein the pinnacle further comprises:

a first arm on a first side of the non-planar base;

a second arm on a second side of the non-planar base opposite the first arm; and a bridge connecting the first arm, the second arm, and the non-planar base.

6. The method of claim 5, wherein:

the distal end of the non-planar base defines a concave intersection between the bridge and the non-planar base, forming an obtuse angle; and the proximal end of the non-planar base defines a concave intersection between the front face and the non-planar base, forming an acute angle.

7. The method of claim 3, wherein the subcutaneous implant is placed within an upper arm of the patient.

8. The method of claim 7, further comprising:

imaging the upper arm of the patient before making the incision in order to verify a subcutaneous location of the subcutaneous implant.

9. The method of claim 3, wherein:

the subcutaneous implant defines an elongated cylindrical body;

the distal end of the non-planar base comprises an indentation dimensioned to receive the leading end of the subcutaneous implant; and the non-planar base is between 3 cm and 6 cm in length.

\* \* \* \* \*